United States Patent
Masuda

(10) Patent No.: US 10,584,138 B2
(45) Date of Patent: Mar. 10, 2020

(54) SALT COMPRISING SILICON-CONTAINING PHOSPHATE ANION, AND LUBRICANT

(71) Applicant: Nisshinbo Holdings, Inc., Tokyo (JP)

(72) Inventor: Gen Masuda, Chiba (JP)

(73) Assignee: NISSHINBO HOLDINGS, INC., Tokyo (JP)

(*) Notice: Subject to any disclaimer, the term of this patent is extended or adjusted under 35 U.S.C. 154(b) by 0 days.

(21) Appl. No.: 16/465,276

(22) PCT Filed: Nov. 30, 2017

(86) PCT No.: PCT/JP2017/043045
§ 371 (c)(1),
(2) Date: May 30, 2019

(87) PCT Pub. No.: WO2018/105482
PCT Pub. Date: Jun. 14, 2018

(65) Prior Publication Data
US 2019/0389889 A1    Dec. 26, 2019

(30) Foreign Application Priority Data

Dec. 5, 2016 (JP) ................... 2016-235862

(51) Int. Cl.
*C07F 9/09* (2006.01)
*C10M 137/04* (2006.01)

(52) U.S. Cl.
CPC .......... *C07F 9/092* (2013.01); *C10M 137/04* (2013.01)

(58) Field of Classification Search
CPC ........ C07F 9/092; C07F 9/091; C10M 137/04
See application file for complete search history.

(56) References Cited

U.S. PATENT DOCUMENTS

| 3,898,257 A | 8/1975 | Gregory |
| 5,380,904 A * | 1/1995 | Chapman ............ A61L 33/0082 128/912 |

| 2008/0076684 A1 | 3/2008 | Nanbu et al. |
| 2009/0029887 A1 | 1/2009 | Schwab et al. |
| 2015/0203518 A1 | 7/2015 | Masuda |
| 2015/0291633 A1 | 10/2015 | Masuda |

FOREIGN PATENT DOCUMENTS

| JP | 6-65266 A | 3/1994 |
| JP | 10-53959 A | 2/1998 |
| JP | 2008-74947 A | 4/2008 |
| JP | 2009-30056 A | 2/2009 |
| JP | 2009-57541 A | 3/2009 |
| JP | 2014-15505 A | 1/2014 |
| JP | 2014-82315 A | 5/2014 |
| WO | 85/03295 A1 | 8/1985 |
| WO | 2013/005712 A1 | 1/2013 |
| WO | 2017/183342 A1 | 10/2017 |

OTHER PUBLICATIONS

International Search Report dated Jan. 30, 2018, issued in counterpart International Application No. PCT/JP2017/043045 (2 pages).
Nishikawa et al., "The Science of ionic liquids—Toward a new generation of liquids", Maruzen Publishing, 2012, pp. 317-322, with English Translation (21 pages). (Cited in Specification).
"Ionic liquid technology", Toray Research Center, Inc., 2013, pp. 67-73, with English Translation (18 pages). (Cited in Specification).

\* cited by examiner

*Primary Examiner* — Jafar F Parsa
(74) *Attorney, Agent, or Firm* — Westerman, Hattori, Daniels & Adrian, LLP

(57) ABSTRACT

Provided is a salt that comprises a silicon-containing phosphate anion represented by formula (1)

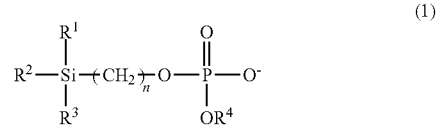

(in the formula, $R^1$-$R^4$ each independently represent an alkyl group having 1-4 carbon atoms, and n represents an integer of 2-8).

12 Claims, 15 Drawing Sheets

SALT COMPRISING SILICON-CONTAINING PHOSPHATE ANION, AND LUBRICANT

TECHNICAL FIELD

The present invention relates to a salt containing a silicon-containing phosphate anion, and a lubricant containing the same.

BACKGROUND ART

The term "ionic liquid" refers to a salt composed solely of ions which generally has a melting point of 100° C. or below. Various applied research is being done on ionic liquids on account of their properties. In particular, given their non-volatility, flame retardancy and high heat resistance, research is even being conducted on the use of ionic liquids as lubricants (see, for example, Patent Documents 1 and 2, and Non-Patent Documents 1 and 2).

Ionic liquids have the physicochemical qualities required of a lubricant. In particular, fluorinated ion-containing ionic liquids such as tetrafluoroborate, hexafluorophosphate and bis(trifluoromethanesulfonyl)imide salts reportedly have excellent anti-wear properties. However, since ionic liquids contain halogen atoms, there are problems of high environmental load, especially concerning environmental problems at the time of leakage, waste disposal, and the like.

In addition, when a fluorine-containing ionic liquid is used as a lubricant, moisture infiltration is a problem. Even the infiltration of a trace amount of moisture sometimes leads to critical defects when this moisture reacts with hydrogen fluoride from fluorinated anions that have decomposed in chemical reactions (tribochemical reactions) activated by friction, causing metallic materials to corrode or polymer materials to deteriorate. Moreover, the hydrogen fluoride generated is strongly toxic and thus dangerous as well. Therefore, fluorine-containing ionic liquids generally have the reputation of being usable as lubricants only in space-related applications where moisture is absent or for ceramics without metal interfaces, and are not currently in practical use as general-purpose lubricants.

PRIOR ART DOCUMENTS

Patent Documents

Patent Document 1: JP-A-2009-57541
Patent Document 2: JP-A-2014-15505

Non-Patent Documents

Non-Patent Document 1: *Ion Ekitai no Kagaku—Shin-sedai Ekitai e no Chōsen*—[The Science of ionic liquids—Toward a new generation of liquids], Maruzen Publishing (2012), pp. 317-322.
Non-Patent Document 2: *Ion Ekitai Tekunorojii* [Ionic liquid technology], Toray Research Center (2013), pp. 67-73.

SUMMARY OF INVENTION

Technical Problem

It is therefore an object of the present invention to provide a novel phosphate not containing a halogen atom, suitably used as a lubricant, an additive for lubricants, or the like.

Solution to Problem

The inventor has conducted extensive investigations aimed at achieving the above object. As a result, he has discovered that a salt containing a predetermined phosphate anion containing a silicon atom (hereinafter, also referred to as a silicon-containing phosphate) has low friction coefficients and is especially useful as a lubricant or an additive for lubricants.

Accordingly, the invention provides the following silicon-containing phosphate, and a lubricant.
1. A salt containing a silicon-containing phosphate anion of formula (1) below:

[Chem. 1]

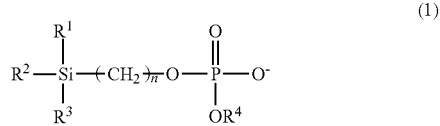

wherein $R^1$ to $R^4$ are each independently an alkyl group of 1 to 4 carbon atoms, and n is an integer of 2 to 8.
2. The salt of 1 above, wherein $R^1$ to $R^3$ are the same group.
3. The salt of 2 above, wherein $R^1$ to $R^3$ are all methyl groups.
4. The salt of any of 1 to 3 above, wherein $R^4$ is a methyl group.
5. The salt of any of 1 to 4 above, wherein n is an integer of 2 to 4.
6. The salt of any of 1 to 5 above, wherein the cation is an organic cation.
7. The salt of any of 1 to 6 above, wherein the cation is a phosphorus atom-containing cation.
8. The salt of any of 1 to 6 above, wherein the cation is a nitrogen atom-containing cation.
9. The salt of any of 1 to 8 above, which is an ionic liquid having a melting point of 100° C. or below.
10. A composition containing the salt of any of 1 to 9 above.
11. A lubricant containing the salt of any of 1 to 9 above.
12. A silicon-containing phosphoric acid ester of formula below:

[Chem. 2]

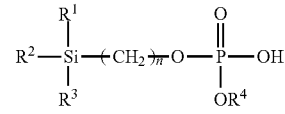

wherein $R^1$ to $R^4$ are each independently an alkyl group of 1 to 4 carbon atoms, and n is an integer of 2 to 8.

Advantageous Effects of Invention

Since the silicon-containing phosphate of the invention is halogen-free, it has a low environmental load. In addition, the ionic liquid consisting of the silicon-containing phosphate of the invention has a low friction coefficient and can be suitably used as a lubricant, and also applied to other uses such as another reaction solvent or electrolyte solvent in which an ionic liquid can be used. The silicon-containing phosphate of the invention can be suitably used not only as an additive for lubricants but also as an antistatic agent or a plasticizer added to polymer materials such as rubber and plastics, or as an electrolyte salt of various electric storage devices.

DESCRIPTION OF EMBODIMENTS

[Silicon-Containing Phosphate]

Figure 1:
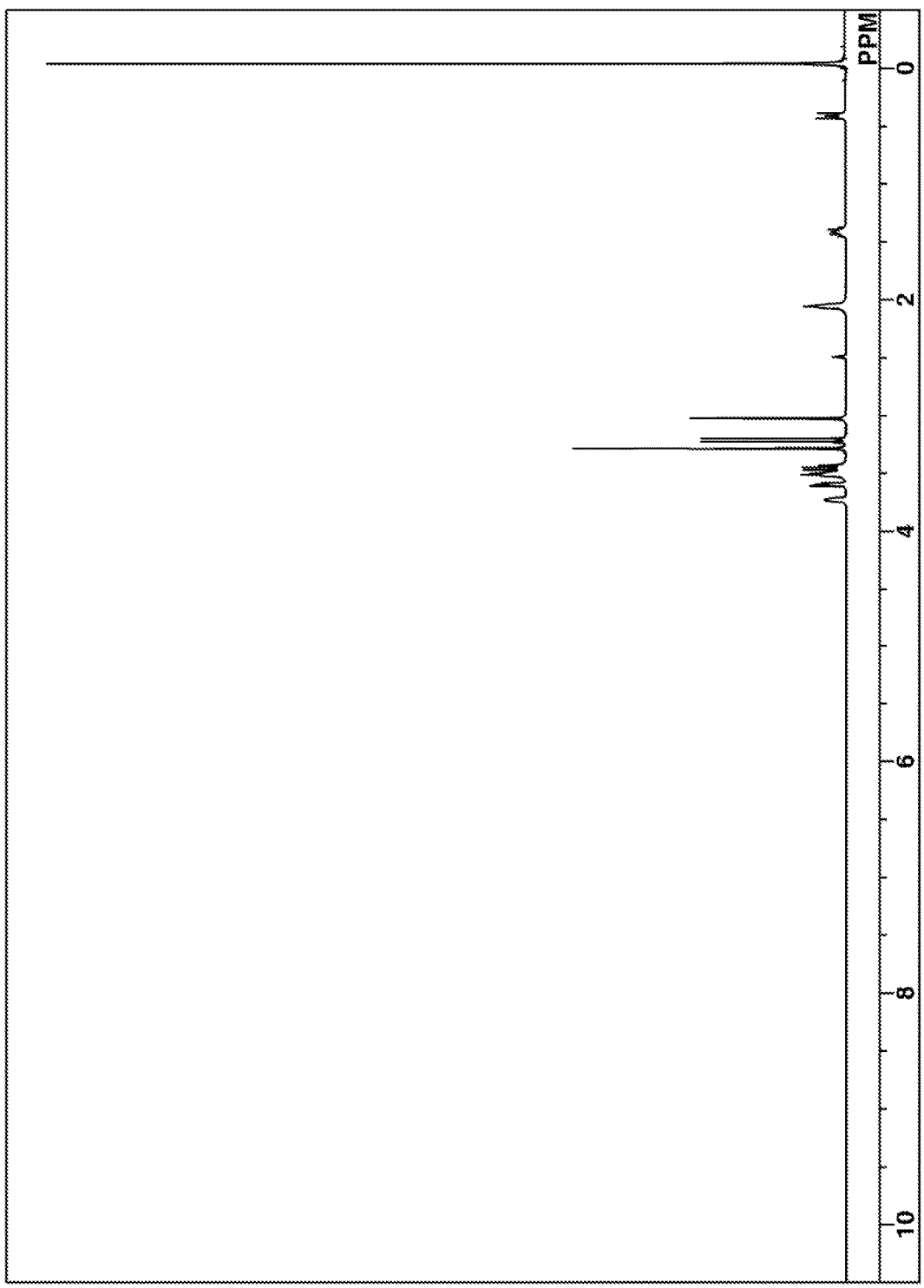
FIG. 1 is the $^1$H-NMR spectrum of Silicon-Containing Phosphate 1 prepared in Working Example 1.

The silicon-containing phosphate of the invention contains a silicon-containing phosphate anion of formula (1) below.

[Chem. 3]

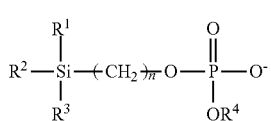

(1)

In the formula, $R^1$ to $R^4$ are each independently an alkyl group of 1 to 4 carbon atoms. The alkyl group may be linear, branched or cyclic. Examples include methyl, ethyl, n-propyl, isopropyl, cyclopropyl, n-butyl, s-butyl, isobutyl, t-butyl, and cyclobutyl groups.

Among them, $R^1$ to $R^3$ are preferably an alkyl group of 1 to 3 carbon atoms, more preferably a linear alkyl group of 1 to 3 carbon atoms, further preferably a methyl group or an ethyl group, and most preferably a methyl group. In addition, $R^1$ to $R^3$ are preferably all the same group, and particularly most preferably all methyl groups. $R^4$ is preferably an alkyl group of 1 to 3 carbon atoms, more preferably a linear alkyl group of 1 to 3 carbon atoms, further preferably a methyl group or an ethyl group, and most preferably a methyl group.

In the formula (1), n is an integer of 2 to 8, and preferably an integer of 2 to 4.

The cation contained in the silicon-containing phosphate of the invention is not particularly limited, and is preferably a monovalent cation. In addition, the cation may be an inorganic cation or an organic cation.

Examples of the inorganic cation include alkali metal ions such as sodium ion, potassium ion and lithium ion, and metal ions such as silver ion, zinc ion and copper ion.

As the organic cation, a phosphorus atom-containing cation or a nitrogen atom-containing cation is preferable, and specifically, a quaternary phosphonium ion, a quaternary ammonium ion, an imidazolium ion, a pyridinium ion, a pyrrolidinium ion, a piperidinium ion or the like is preferable.

As the phosphorus atom-containing cation, for example, a quaternary phosphonium ion of formula (2) below is preferable.

[Chem. 4]

(2)

In the formula (2), $R^{11}$ is an alkyl group of 1 to 20 carbon atoms. The alkyl group of 1 to 20 carbon atoms may be linear, branched, or cyclic. Examples include, in addition to the above-described alkyl groups of 1 to 4 carbon atoms, n-pentyl, cyclopentyl, n-hexyl, cyclohexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, and n-eicosyl groups.

In the formula (2), $R^{12}$ is an alkyl group of 1 to 20 carbon atoms or an alkoxyalkyl group of —(CH$_2$)$_k$—OR. k is 1 or 2. R is a methyl group or an ethyl group. Examples of the alkyl group of 1 to 20 carbon atoms include those described above.

Among the quaternary phosphonium ions of the formula (2), those in which $R^{12}$ is an alkoxyalkyl group of —(CH$_2$)$_k$—OR are likely to form an ionic liquid. When $R^{12}$ is an alkyl group, those having a structure in which $R^{11}$ and $R^{12}$ are different are likely to form an ionic liquid. In this case, the difference in carbon number is preferably 1 or more, more preferably 3 or more, and further preferably 5 or more.

As the nitrogen atom-containing cation, for example, one represented by formula (3) below is preferable.

[Chem. 5]

(3)

In the formula (3), $R^{21}$ to $R^{24}$ are each independently an alkyl group of 1 to 20 carbon atoms or an alkoxyalkyl group of —$(CH_2)_k$—OR. k is 1 or 2. R is a methyl group or an ethyl group. When $R^{21}$ to $R^{24}$ are all alkyl groups, those in which at least one of $R^{21}$ to $R^{24}$ has a structure different from the others are likely to form an ionic liquid, in which case the difference in carbon number is preferably 1 or more, more preferably 3 or more, and further preferably 5 or more.

Examples of the alkyl group of 1 to 20 carbon atoms include the same ones as those described above. Examples of the alkoxyalkyl group include methoxymethyl, ethoxymethyl, methoxyethyl, and ethoxyethyl groups. Among the alkoxyalkyl groups, a methoxymethyl group or a methoxyethyl group is preferable.

Also, any two of $R^{21}$ to $R^{24}$ may be bonded to each other to form a ring with a nitrogen atom to which they are bonded, and further, the remaining two may also be bonded to each other to form a spiro ring having a nitrogen atom as a spiro atom. In this case, examples of the ring include an aziridine ring, an azetidine ring, a pyrrolidine ring, a piperidine ring, an azepane ring, an imidazolidine ring, a pyridine ring, a pyrrole ring, an imidazole ring and a quinol ring, and a pyrrolidine ring, a piperidine ring, an imidazolidine ring, a pyridine ring, a pyrrole ring, an imidazole ring, a quinol ring or the like is preferable, and a pyrrolidine ring, an imidazolidine ring or the like is more preferable. Also, as the spiro ring, a 1,1'-spirobipyrrolidine ring is particularly preferable.

Specific examples of the nitrogen atom-containing cation of the formula (3) include quaternary ammonium ions of formula (3-1) or (3-2) below, and pyrrolidinium ions of formula (3-3) or (3-4) below.

[Chem. 6]

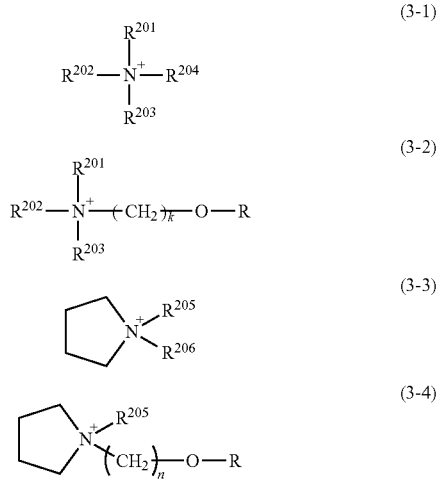

In the formulas (3-1) to (3-4), R and k are as defined above. $R^{201}$ to $R^{204}$ are each independently an alkyl group of 1 to 4 carbon atoms. $R^{205}$ and $R^{206}$ are each independently an alkyl group of 1 to 4 carbon atoms. Also, $R^{205}$ and $R^{206}$ may be bonded to each other to form a ring with a nitrogen atom to which they are bonded.

As the nitrogen atom-containing cation, for example, an imidazolium ion of formula (4) below is also preferable.

[Chem. 7]

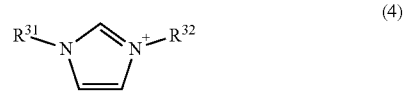

In the formula (4), $R^{31}$ and $R^{32}$ are each independently an alkyl group of 1 to 20 carbon atoms or an alkoxyalkyl group of —$(CH_2)_k$—OR. R and k are as defined above. Examples of the alkyl group and alkoxyalkyl group of 1 to 20 carbon atoms include the same ones as those exemplified as $R^{21}$ to $R^{24}$. In this case, it is more likely to form an ionic liquid if $R^{31}$ and $R^{32}$ are different groups.

As the nitrogen atom-containing cation, for example, a pyridinium ion of formula (5) below is also preferable.

[Chem. 8]

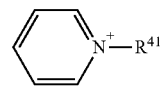

In the formula (5), $R^{41}$ is an alkyl group of 1 to 8 carbon atoms or an alkoxyalkyl group of —$(CH_2)_k$—OR. R and k are as defined above.

The alkyl group of 1 to 8 carbon atoms may be linear, branched, or cyclic. Examples include methyl, ethyl, n-propyl, isopropyl, cyclopropyl, n-butyl, s-butyl, isobutyl, t-butyl, cyclobutyl, n-pentyl, cyclopentyl, n-hexyl, cyclohexyl, n-heptyl, and n-octyl groups. Examples of the alkoxyalkyl group include the same ones as those exemplified as $R^{21}$ to $R^{24}$.

The silicon-containing phosphate of the invention becomes an ionic liquid depending on the type of cation. For example, the one in which the cation is represented by the formula (3-4) becomes an ionic liquid, and among those represented by the formula (2), those having a structure in which $R^{11}$ and $R^{12}$ are different from each other are likely to be an ionic liquid. Since the ionic liquid consisting of the silicon-containing phosphate of the invention is halogen-free, it has a low environmental load and exhibits excellent lubricant performance. In particular, the salt of the invention having a quaternary phosphonium ion of the formula (2) has high heat resistance as compared with conventional halogen-free salts and is particularly excellent in lubricant performance.

[Method for Producing Silicon-Containing Phosphate]

The silicon-containing phosphate of the invention can be synthesized, for example, according to Scheme A below.

Scheme A

[Chem. 9]

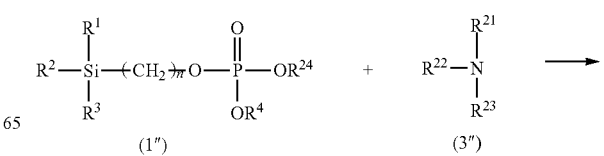

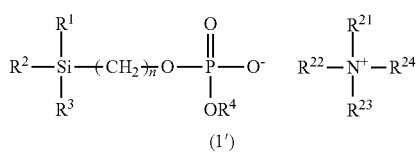

(1')

In the formula, $R^1$ to $R^4$, $R^{21}$ to $R^{24}$ and n are as described above, and it is preferable in the above reaction that $R^{24}$ is an alkyl group of 1 to 4 carbon atoms. That is, when the cation is one represented by formula (3-2) or formula (3-4), it is preferable to use one represented by formula (1''') below as the compound of the formula (1''), and use one represented by formula (3-2') or formula (3-4') below as the compound of formula (3'). The compound of the formula (3-2') or formula (3-4') below can be synthesized by a conventionally known method.

[Chem. 10]

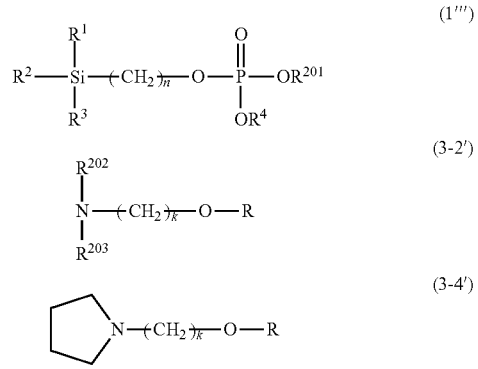

wherein $R^1$ to $R^4$, $R^{201}$ to $R^{203}$, n and k are as defined above.

In the reaction shown in Scheme A, the use ratio of the compound of the formula (1'') and the compound of the formula (3') is not particularly limited, and in consideration of cost, it is preferably performed at a ratio close to 1:1. However, in order to complete the reaction more quickly, to eliminate residual raw materials and to simplify an isolation step, the reaction may be performed by excessively using one component. In that case, it is preferable to excessively use a component that is easy to remove.

The reaction shown in Scheme A is preferably carried out without a solvent, and a solvent may be used. The solvent usable in this case is not particularly limited, provided that it does not hinder the progress of the reaction, and a general-purpose solvent may be appropriately used.

The reaction temperature is usually about 60 to 120° C., and preferably about 80 to 100° C. The reaction time may be appropriately determined according to the progress of the reaction, and is not particularly limited, and usually it mostly reacts in several hours to ten and several hours. For the purpose of not leaving residual raw materials, the reaction may be continued for a longer time.

The compound of the formula (1'') which is a starting material may be synthesized by a known method, for example, it can be synthesized according to Scheme B below.

Scheme B

[Chem. 11]

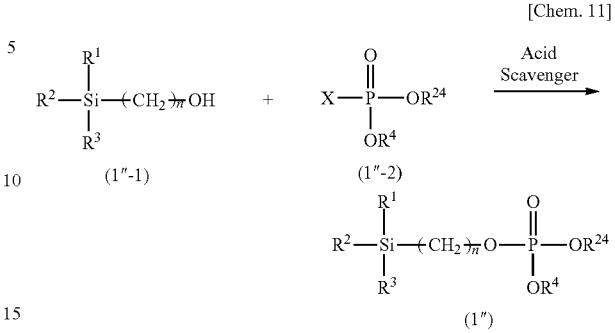

Herein $R^1$ to $R^4$, $R^{24}$ and n are as defined above, and X is a halogen atom such as a chlorine atom, a bromine atom or an iodine atom.

As the compound of formula (1''-1) and the compound of formula (1''-2), a commercially available product can be used. The compound of the formula (1''-1) may be reacted with the compound of the formula (1''-2) in the presence of an acid scavenger according to a usual phosphate ester synthesis method.

The reaction shown in Scheme B can be carried out without a solvent, and a general purpose solvent may be used.

In Scheme A, a case where the cation is a quaternary ammonium ion of the formula (3) has been cited as an example, and when synthesizing the silicon-containing phosphate of the invention in which the cation is a quaternary phosphonium ion of the formula (2), it can be synthesized in the same way as in Scheme A, using a trialkylphosphine which can give the quaternary phosphonium ion, instead of the compound of the formula (3'). Also, the silicon-containing phosphate of the invention wherein the cation is an imidazolium ion of the formula (4) or a pyridinium ion of the formula (5) can be synthesized in the same way as in Scheme A, using 1-alkylimidazole which can give the imidazolium ion or pyridine, instead of the compound of the formula (3').

The silicon-containing phosphate of the invention can also be produced by a neutralization method using an ion exchange resin, using an arbitrary salt containing a silicon-containing phosphate anion of the formula (1) and a salt containing the above-described cation. For example, when synthesizing a salt in which the cation is a quaternary phosphonium ion of the formula (2), it can be produced by using a silicon-containing phosphate of the above-described formula (1') and a salt of formula (2') below.

[Chem. 12]

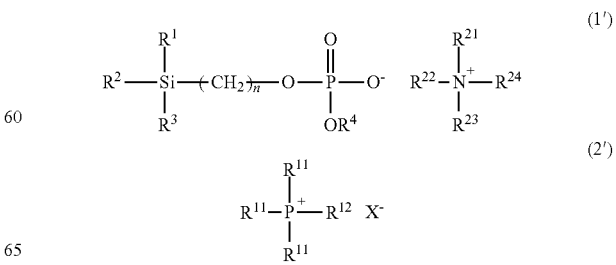

wherein $R^1$ to $R^4$, $R^{11}$, $R^{12}$, $R^{21}$ to $R^{24}$ and n are as defined above, and $X^-$ is an arbitrary anion.

The silicon-containing phosphate of the formula (1') can be synthesized according to the above-described method. The salt of the formula (2') can be synthesized according to a conventionally known method, or a commercially available product can be used.

In this neutralization method, the silicon-containing phosphate of the formula (1') and the salt of the formula (2') may be first converted to a silicon-containing phosphoric acid ester of formula below and a hydroxide using a cation exchange resin and an anion exchange resin, respectively, and then both may be mixed.

[Chem. 13]

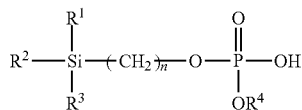

wherein $R^1$ to $R^4$ and n are as defined above.

In the invention, when this neutralization method is applied, a counter ion is not particularly limited, provided that the salt of the formula (2') is ion-exchanged. However, in terms of cost, a halide ion is preferable as the counter ion, and in terms of cost, a chloride ion or a bromide ion is particularly preferable.

The molar ratio of the silicon-containing phosphoric acid ester and the hydroxide in the neutralization reaction is not particularly limited, and it can usually be about 5:1 to 1:5. In consideration of cost, it is preferable to perform at a ratio close to 1:1, and it is particularly preferable to set a neutralization point of an aqueous layer as a reaction termination point. After completion of the reaction, a target substance can be obtained by performing usual post-treatment.

Examples of other method for producing the silicon-containing phosphate include an ion exchange method using an ion exchange resin, using the silicon-containing phosphate of the formula (1') and the salt of the formula (2').

Specifically, as an ion exchange method, first, an aqueous solution of the salt of the formula (1') is passed through a column packed with a cation exchange resin, a cation of the salt is supported on a cation exchange resin, and water is passed through to wash the column. Next, the salt of the formula (2') is passed through the column, and an eluate is recovered and purified, thereby a target silicon-containing phosphate can be produced.

As the cation exchange resin, a commonly used cation exchange resin can be used, and a strongly acidic cation exchange resin is preferably used. These are available as commercial products.

In addition, it is possible to synthesize the silicon-containing phosphate of the invention also by, other than the synthesis method described above, a general ionic liquid synthesis method described in books (*Ionsei Ekitai—Kaihatsu no Saizensen to Mirai*—[Ionic Liquid—Frontier of Development and Future—], CMC Publishing Co., Ltd. (2003), *Ion Ekitai II—Kyouitekina Shinpo to Tasaina Kinmirai*—[Ionic Liquid II—Marvelous Developments and Colorful Near Future—], CMC Publishing Co., Ltd. (2006), or the like). For example, it can be also produced by reacting the salt of the formula (2') with the silicon-containing phosphate of the formula (1') in a solvent. In this case, the solvent may be either water or an organic solvent. The solvent may be selected, in consideration of the ease of isolation and purification of the product, and the like.

[Lubricant]

When the silicon-containing phosphate of the invention is an ionic liquid, itself can be used as a lubricant. Since the ionic liquid has a low friction coefficient and small fluctuation, it can be suitably used as a lubricant. Moreover, because the ionic liquid does not form substances such as hydrogen fluoride that exhibit toxicity, there is no possibility that it will cause the deterioration of metallic materials, polymer materials and the like. This ionic liquid can therefore be adapted to a variety of uses as a general-purpose lubricant.

The lubricant of the invention may consist entirely of the above ionic liquid, although it may include an additive or additives as well. The additive is not particularly limited, provided that it is a substance that dissolves in the above-described ionic liquid. Conventional ionic liquids which include a fluorine-containing anion such as $NTf_2^-$, $BF_4^-$ or $PF_6^-$ have little ability to dissolve an additive generally used as an additive for lubricating oils, making it difficult to improve the tribological properties. However, the above-described silicon-containing ionic liquid is able to dissolve such additives, thus making it possible to cost-effectively improve the tribological properties of the ionic liquid.

Such additives are exemplified by surfactants, dispersants, antioxidants, anti-wear agents, rust inhibitors, corrosion inhibitors, friction modifiers, extreme pressure additives, antifoam agents, viscosity modifiers, and pour point depressants.

Exemplary surfactants include sulfonate surfactants such as alkyl sulfonates and alkylbenzene sulfonates, salicylate surfactants, phosphate surfactants and phenate surfactants. When a surfactant is included, the content thereof is preferably from 0.1 to 10 wt % of the lubricant.

Exemplary dispersants include polyalkenyl succinimides, esters of polyalkenylsuccinic acids, Mannich base and organic phosphoric acid esters. When a dispersant is included, the content thereof is preferably from 0.1 to 10 wt % of the lubricant.

Exemplary antioxidants include zinc dithiophosphate, phenolic antioxidants, aromatic amine-type antioxidants, organosulfur compound-type antioxidants, hindered phenols and phosphite antioxidants. When an antioxidant is included, the content thereof is preferably from 0.1 to 10 wt % of the lubricant.

Exemplary anti-wear agents include phosphorus-based anti-wear agents, sulfur-based anti-wear agents, boric acid derivatives, chlorine-based anti-wear agents, and zinc dithiophosphate. When an anti-wear agent is included, the content thereof is preferably from 0.1 to 10 wt % of the lubricant.

Exemplary rust inhibitors include sulfonates, polyhydric alcohol esters, and alkyl amines. When a rust inhibitor is included, the content thereof is preferably from 0.1 to 10 wt % of the lubricant.

Exemplary corrosion inhibitors include nitrogen-containing compounds such as benzotriazole compounds. When a corrosion inhibitor is included, the content thereof is preferably from 0.1 to 10 wt % of the lubricant.

Exemplary friction modifiers include glycerol fatty acid esters such as glycerol monooleate, and alkyl amines such as oleyl amine. When a friction modifier is included, the content thereof is preferably from 0.1 to 10 wt % of the lubricant.

Exemplary extreme pressure additives include sulfur-based extreme pressure additives such as sulfurized oils and fats, sulfurized olefins, dibenzyl disulfide and dialkyl disulfides, and also phosphorus-based extreme pressure additives. When an extreme pressure additive is included, the content thereof is preferably from 0.1 to 10 wt % of the lubricant.

Exemplary antifoam agents include silicone-type antifoam agents such as polymethylsiloxane. When an antifoam agent is included, the content thereof is preferably from 0.1 to 10 wt % of the lubricant.

Exemplary viscosity modifiers include hydrocarbon-type viscosity modifiers such as polyisobutylene, olefin copolymers and styrene/isoprene copolymers; and ester-type viscosity modifiers such as styrene esters and polymethacrylates. When a viscosity modifier is included, the content thereof is preferably from 0.1 to 10 wt % of the lubricant.

Exemplary pour point depressants include alkylated aromatic compounds, styrene/maleate copolymers and polymethacrylates. When a pour point depressant is included, the content thereof is preferably from 0.1 to 10 wt % of the lubricant.

Of these additives, including a friction modifier or an anti-wear agent is preferred from the standpoint of enabling the tribological properties to be controlled to a high degree.

The silicon-containing phosphate of the invention can also be used as an additive for lubricants. In this case, the silicon-containing phosphate of the invention may or may not be an ionic liquid. By adding the silicon-containing phosphate of the invention to a lubricant, the friction coefficient can be lowered.

[Other Uses]

The silicon-containing phosphate of the invention can be also used as an electrolyte solvent, an electrolyte and an additive for electrolytes for electric storage devices such as electric double layer capacitors, lithium ion capacitors, redox capacitors, lithium secondary batteries, lithium ion secondary batteries, lithium air batteries, and proton polymer batteries. Furthermore, the silicon-containing phosphate of the invention can also be used as an antistatic agent or a plasticizer added to polymer materials such as rubber and plastics. In addition, since the ionic liquid consisting of the silicon-containing phosphate of the invention is a halogen-free ionic liquid, it is useful as a green solvent with a lower environmental load.

EXAMPLES

Working Examples and Comparative Examples are given below by way of illustration, although the invention is not limited by these Examples. In formulas below, "Me" represents a methyl group.

[1] Synthesis of Silicon-Containing Phosphate

[Synthesis Example 1] Synthesis of Compound 1

[Chem. 14]

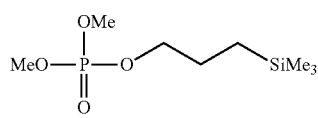

Compound 1

3-Trimethylsilyl-1-propanol (Kanto Chemical Co., Ltd.) in an amount of 1.00 part by weight and 1.21 parts by weight of dimethyl chlorophosphate (Sigma-Aldrich Co.) were added to a reaction vessel, and 0.66 parts by weight of pyridine (Wako Pure Chemical Industries, Ltd.) was slowly added dropwise thereto, with stirring under ice cooling. After completion of the dropwise addition, the reaction solution was stirred overnight as it was, and water was added to the reaction solution to terminate the reaction. Ethyl acetate (Wako Pure Chemical Industries, Ltd.) was added thereto, and extraction was carried out twice. The collected organic layer was washed with saturated brine and then dehydrated using magnesium sulfate (Wako Pure Chemical Industries, Ltd.). After filtration under reduced pressure, the filtrate was concentrated with an evaporator, and the residue was transferred to another vessel and subjected to vacuum distillation. A fraction with a boiling point of 105 to 6° C./3 mmHg was taken to obtain 1.06 parts by weight of a target substance, Compound 1 (yield 59%).

[Working Example 1] Synthesis of Silicon-Containing Phosphate 1

[Chem. 15]

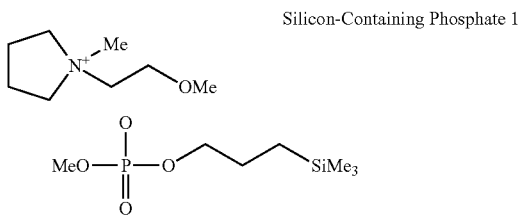

Silicon-Containing Phosphate 1

Pyrrolidine (Wako Pure Chemical Industries, Ltd.) in an amount of 1.51 parts by weight and 1.00 part by weight of 2-methoxyethyl chloride (Kanto Chemical Co., Inc.) were mixed and reacted under reflux for 5 hours. After the reaction, the reaction solution separated into two layers, but when it was allowed to cool for a while, the lower layer solidified. Only the upper layer was recovered by decantation, and purified by vacuum distillation. By the distillation, 0.96 parts by weight of a target substance, N-2-methoxyethylpyrrolidine (boiling point 76° C./vapor pressure 45 mmHg) was obtained (yield 70%).

Compound 1 in an amount of 1.65 parts by weight was added to 1.00 part by weight of the obtained N-2-methoxyethylpyrrolidine, and the mixture was reacted at 100° C. for 5 hours with stirring. After returning the reaction solution to room temperature, a small amount of ethyl acetate was added to lower the viscosity and transferred to a separatory funnel. When hexane was added thereto, the resulting solution separated into two layers. An operation of taking the lower layer, adding a small amount of ethyl acetate to lower the viscosity and transferring to the separatory funnel was repeated twice more, and the lower layer was washed. The lower layer was vacuum-dried to obtain almost quantitatively (1.53 parts by weight, yield 99%) a target substance, Silicon-Containing Phosphate 1 (liquid at room temperature). FIG. 1 shows the $^1$H-NMR spectrum of the obtained Silicon-Containing Phosphate 1 (AL-400 spectrometer from JEOL, Ltd.; solvent, deuterated dimethyl sulfoxide, the same applies hereinafter).

[Working Example 2] Synthesis of Silicon-Containing Phosphate 2

[Chem. 16]

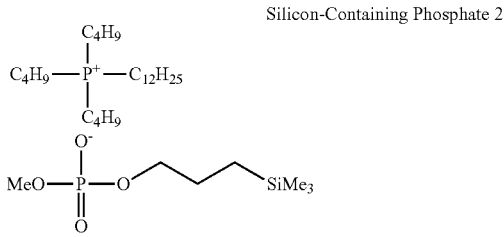

Silicon-Containing Phosphate 2

A 12 mL methanol solution of 4.0 g of tributyldodecylphosphonium bromide (Tokyo Chemical Industry Co., Ltd.) was added to 16 mL (volume containing methanol, the same applies hereinafter) of an anion exchange resin (DS-2, Organo Corporation) washed with deionized water and then solvent-substitution with methanol (Wako Pure Chemical Industries, Ltd.), and the mixture was allowed to stand overnight. DS-2 was filtered off, then the filtrate was added to 16 mL of newly prepared washed and methanol-substituted DS-2. After standing overnight, DS-2 was filtered off. Next, the filtrate was passed through a column packed with 32 mL of DS-2 (eluent: methanol), the filtrate in the range showing alkalinity was collected to obtain a methanol solution of tributyldodecylphosphonium hydroxide in which the bromide was completely substituted with hydroxide.

An aqueous solution of 4.5 g of Silicon-Containing Phosphate 1 dissolved in 18 mL of water was added to 17 mL (volume containing deionized water, the same applies hereinafter) of a cation exchange resin (Amberlyst 15JS-HG•DRY, Organo Corporation) washed with deionized water, and the mixture was stirred for 6 hours. After 15JS-HG•DRY was filtered off, the filtrate was added to 17 mL of newly prepared washed 15JS-HG•DRY. After stirring overnight, 15JS-HG•DRY was filtered off to obtain a cloudy filtrate. The filtrate was transferred to a separatory funnel and extracted with ethyl acetate. The separated aqueous layer was extracted again with ethyl acetate, and each extract (organic layer) was collected and washed three times with water to obtain an ethyl acetate solution of an acid consisting of an anion of Silicon-Containing Phosphate 2 in which the cationic part was completely substituted with hydrogen.

Figure 2:
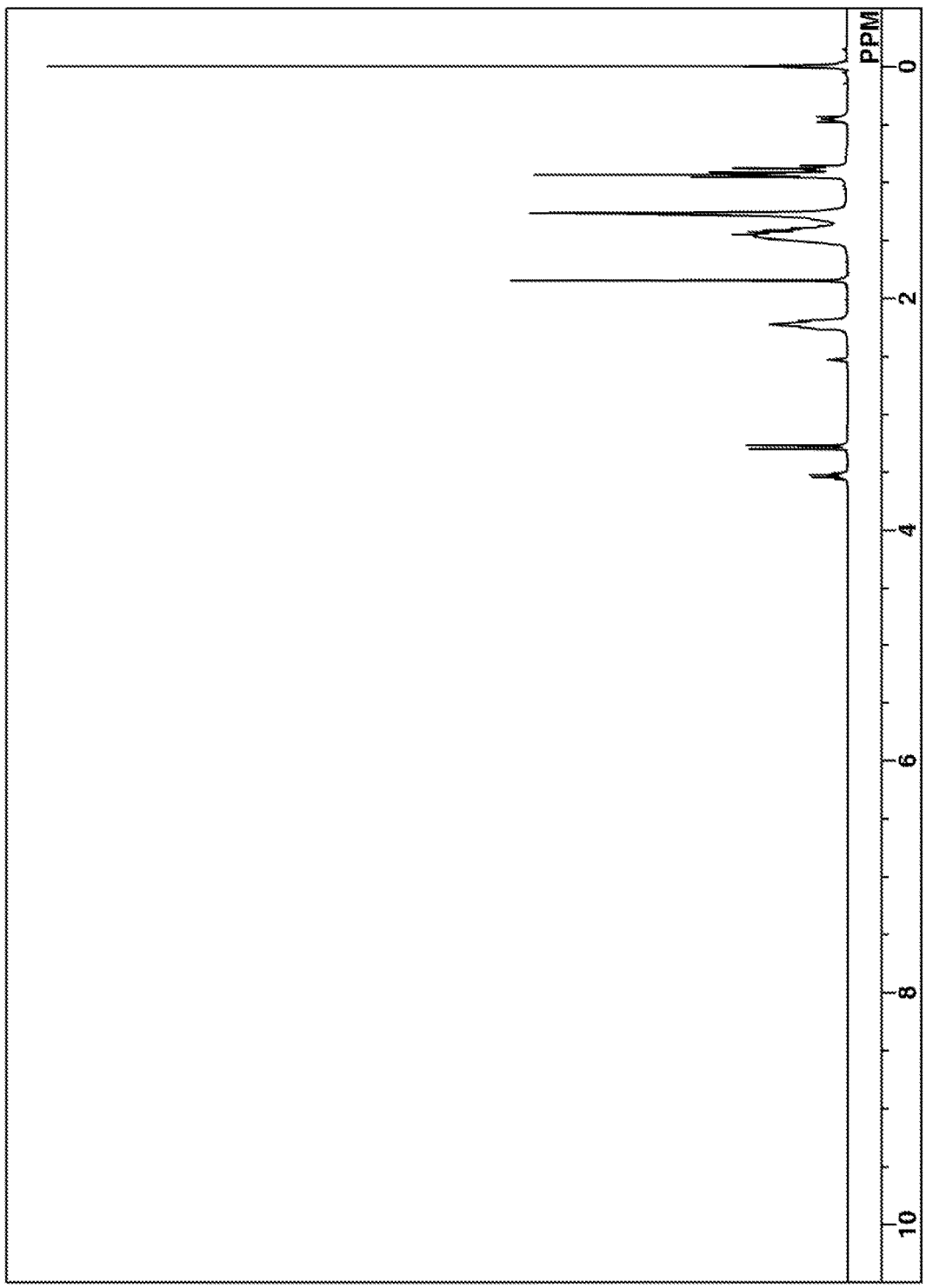
FIG. 2 is the $^1$H-NMR spectrum of Silicon-Containing Phosphate 2 prepared in Working Example 2.

The methanol solution of tributyldodecylphosphonium hydroxide and the ethyl acetate solution of an acid consisting of an anion of Silicon-Containing Phosphate 2 were mixed so that the pH was in the range of 6 to 8. The solvent was removed from the mixed solution by using an evaporator at the beginning and then with a vacuum pump to obtain a target substance, Silicon-Containing Phosphate 2 (yield 4.3 g, yield 81% based on tributyldodecylphosphonium bromide) as a viscous liquid. FIG. 2 shows the $^1$H-NMR spectrum of the obtained Silicon-Containing Phosphate 2.

[Working Example 3] Synthesis of Silicon-Containing Phosphate 3

[Chem. 17]

Silicon-Containing Phosphate 3

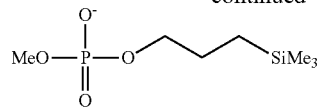

Figure 3:
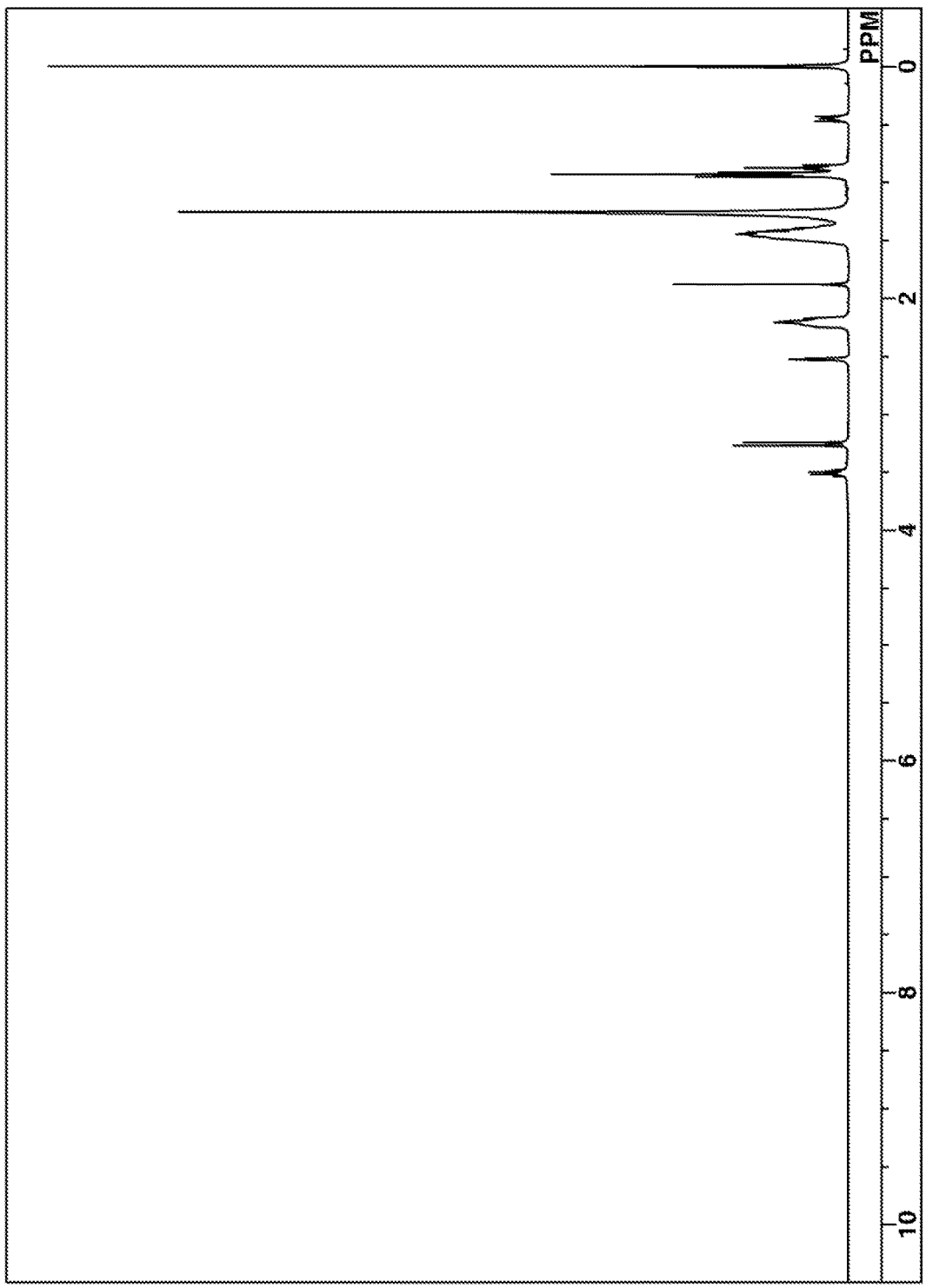
FIG. 3 is the $^1$H-NMR spectrum of Silicon-Containing Phosphate 3 produced in Working Example 3.

Aside from changing tributyldodecylphosphonium bromide to tributylhexadecylphosphonium bromide (Tokyo Chemical Industry Co., Ltd.), Silicon-Containing Phosphate 3 (liquid at room temperature) (yield 93%) was obtained in the same way as in Working Example 2. FIG. 3 shows the $^1$H-NMR spectrum of the obtained Silicon-Containing Phosphate 3.

[Working Example 4] Synthesis of Silicon-Containing Phosphate 4

[Chem. 18]

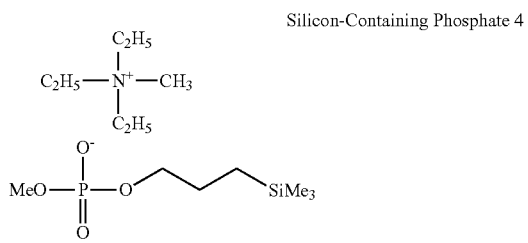

Silicon-Containing Phosphate 4

Figure 4:
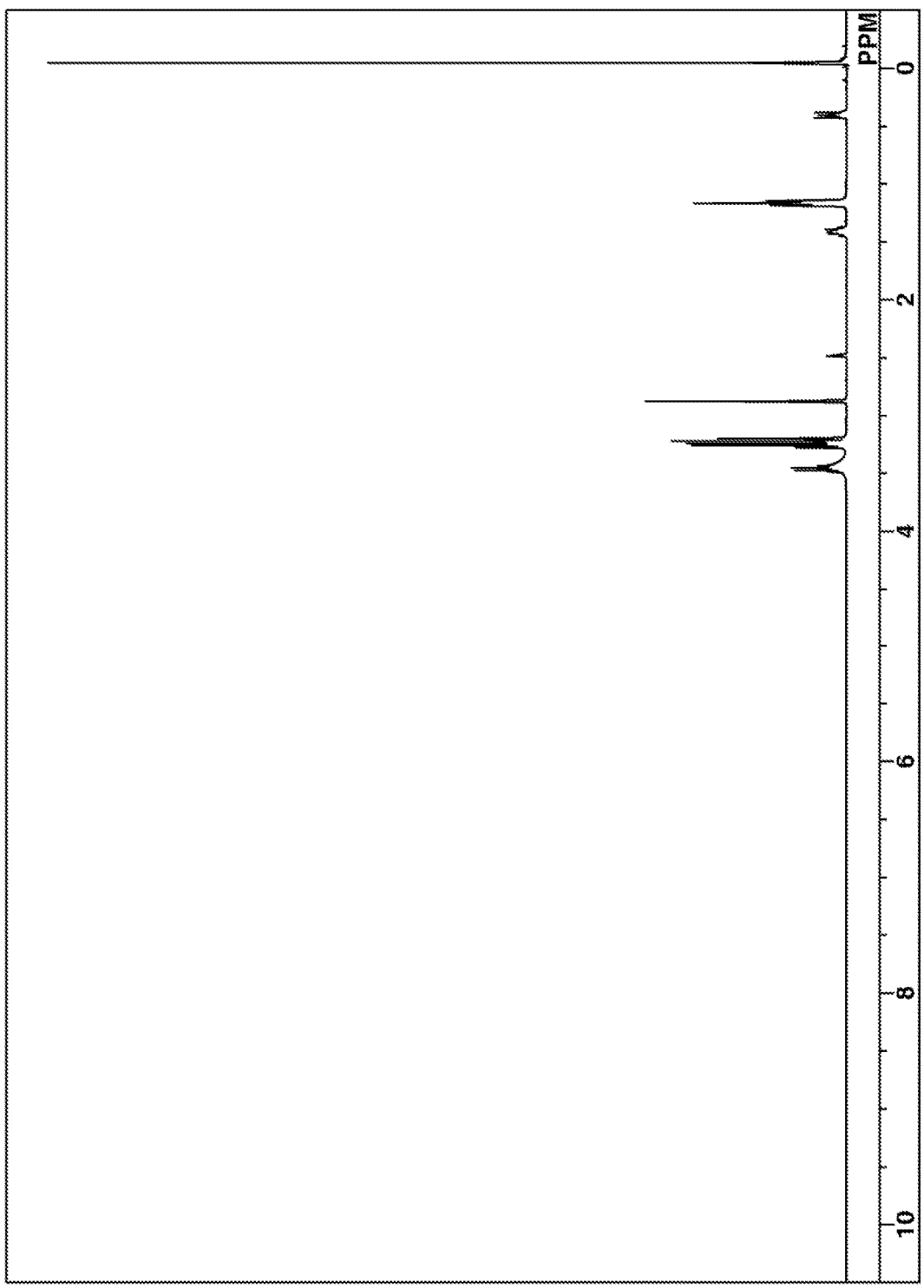
FIG. 4 is the $^1$H-NMR spectrum of Silicon-Containing Phosphate 4 prepared in Working Example 4.
Figure 5:
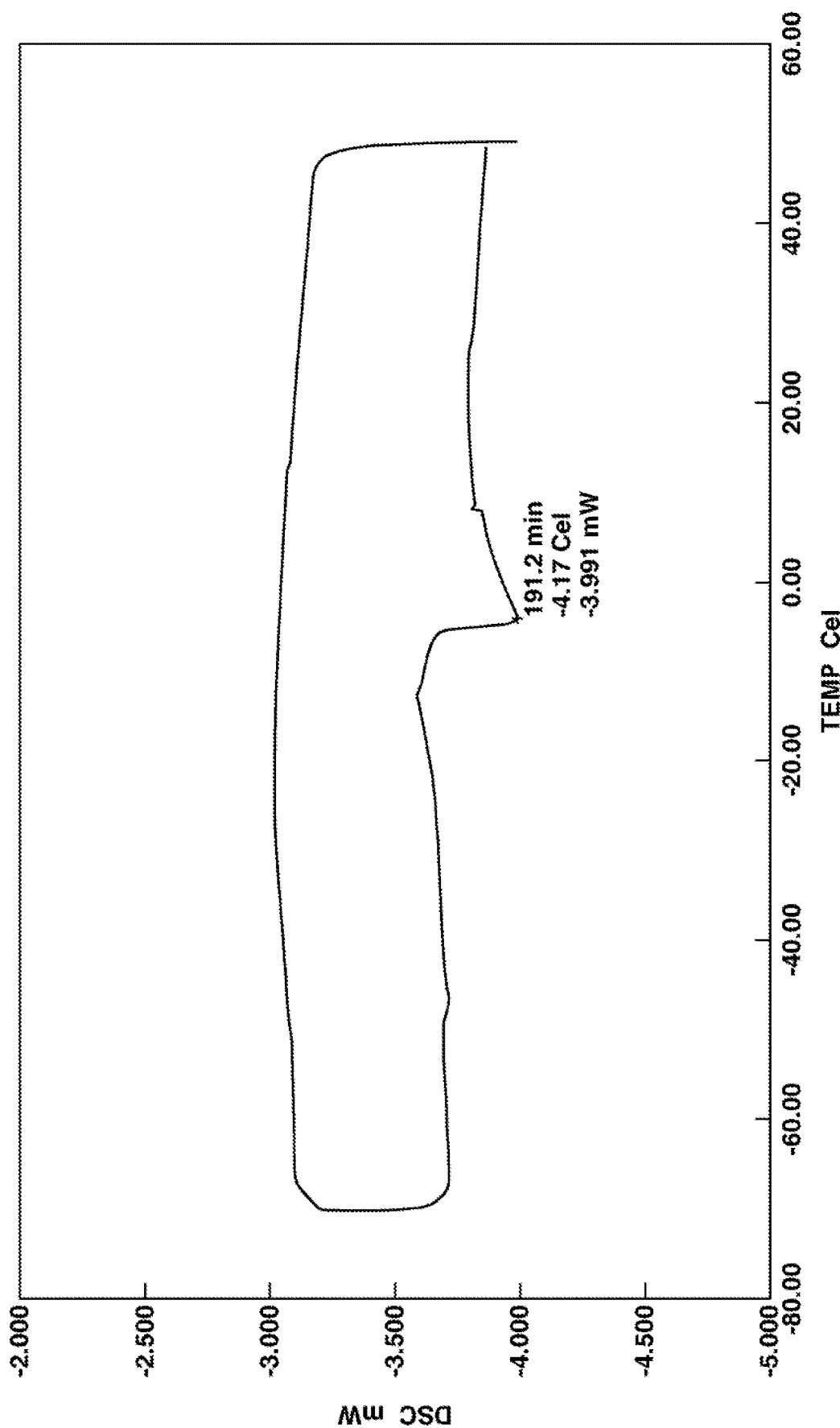
FIG. 5 is the DSC chart of Silicon-Containing Phosphate 1 prepared in Working Example 1.
Figure 6:
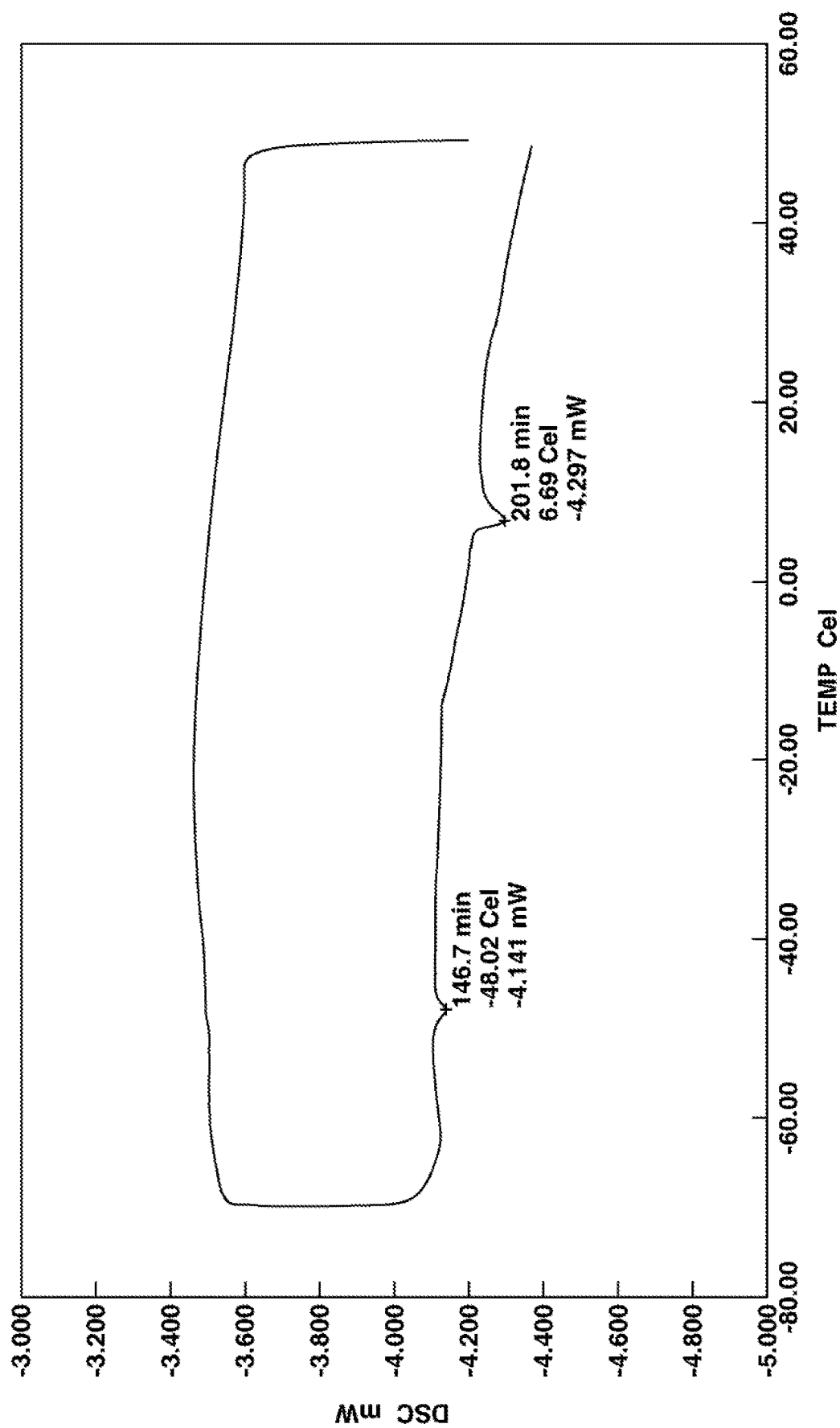
FIG. 6 is the DSC chart of Silicon-Containing Phosphate 2 prepared in Working Example 2.
Figure 7:
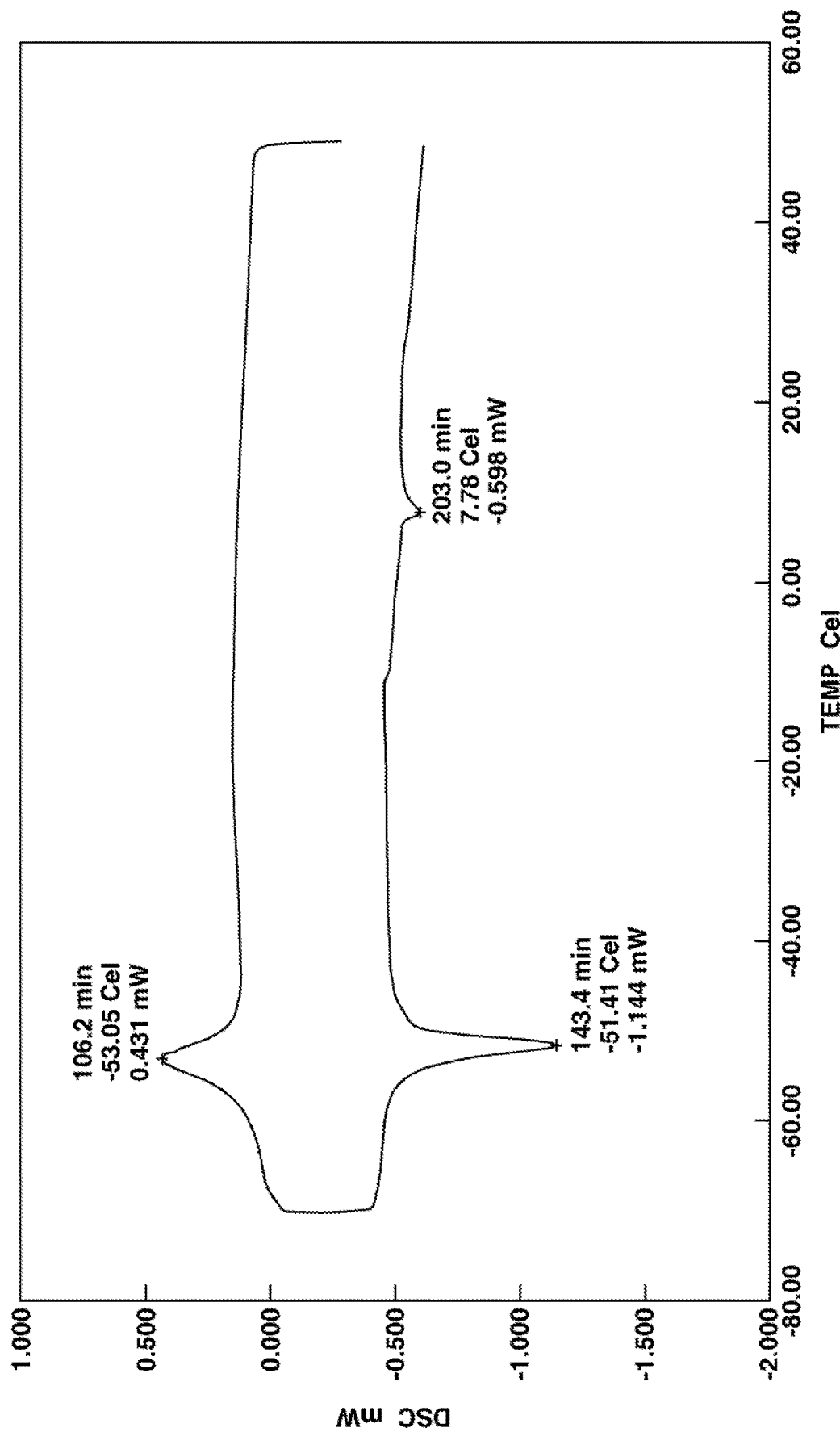
FIG. 7 is the DSC chart of Silicon-Containing Phosphate 3 prepared in Working Example 3.
Figure 8:
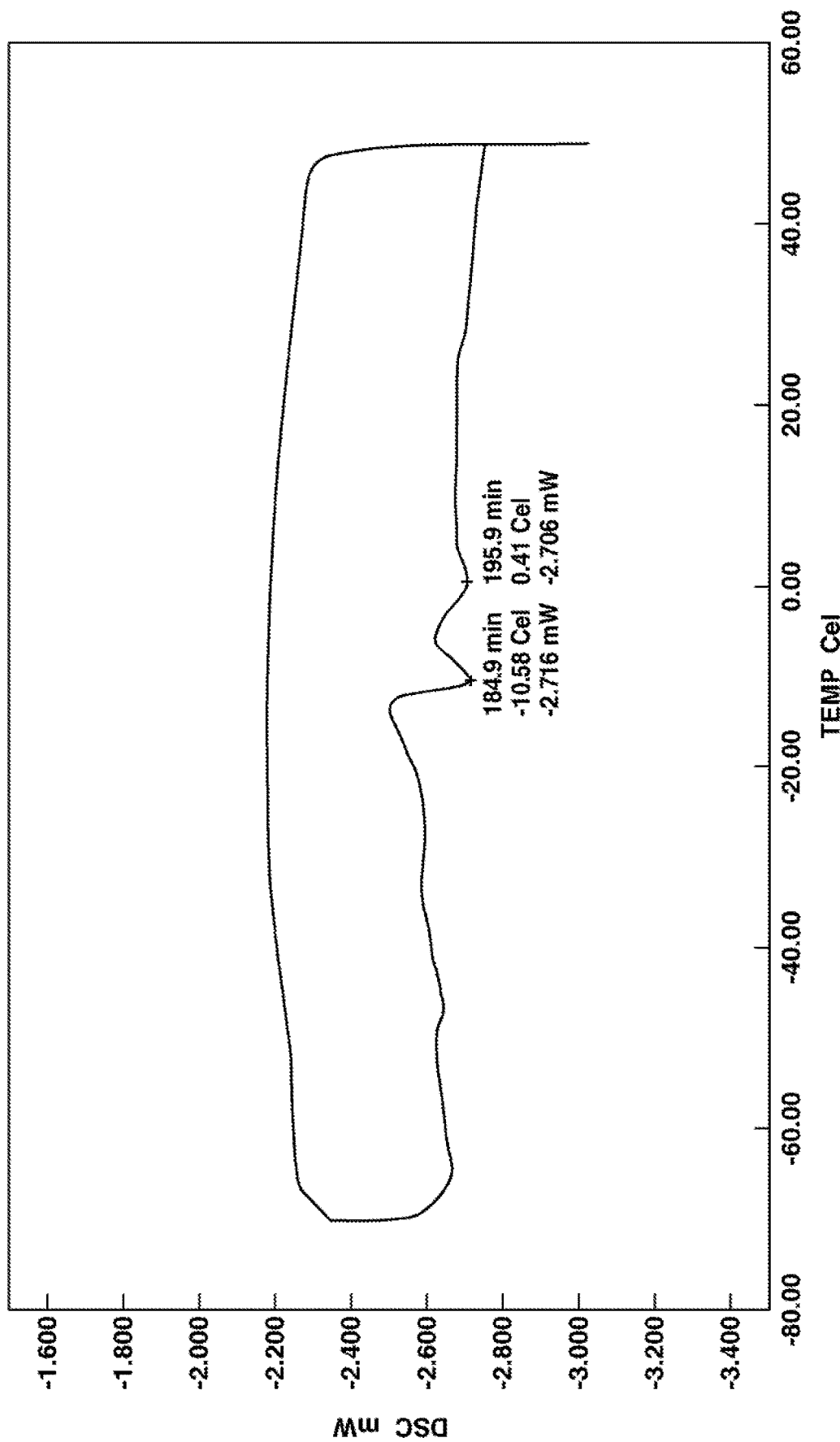
FIG. 8 is the DSC chart of Silicon-Containing Phosphate 4 prepared in Working Example 4.
Figure 9:
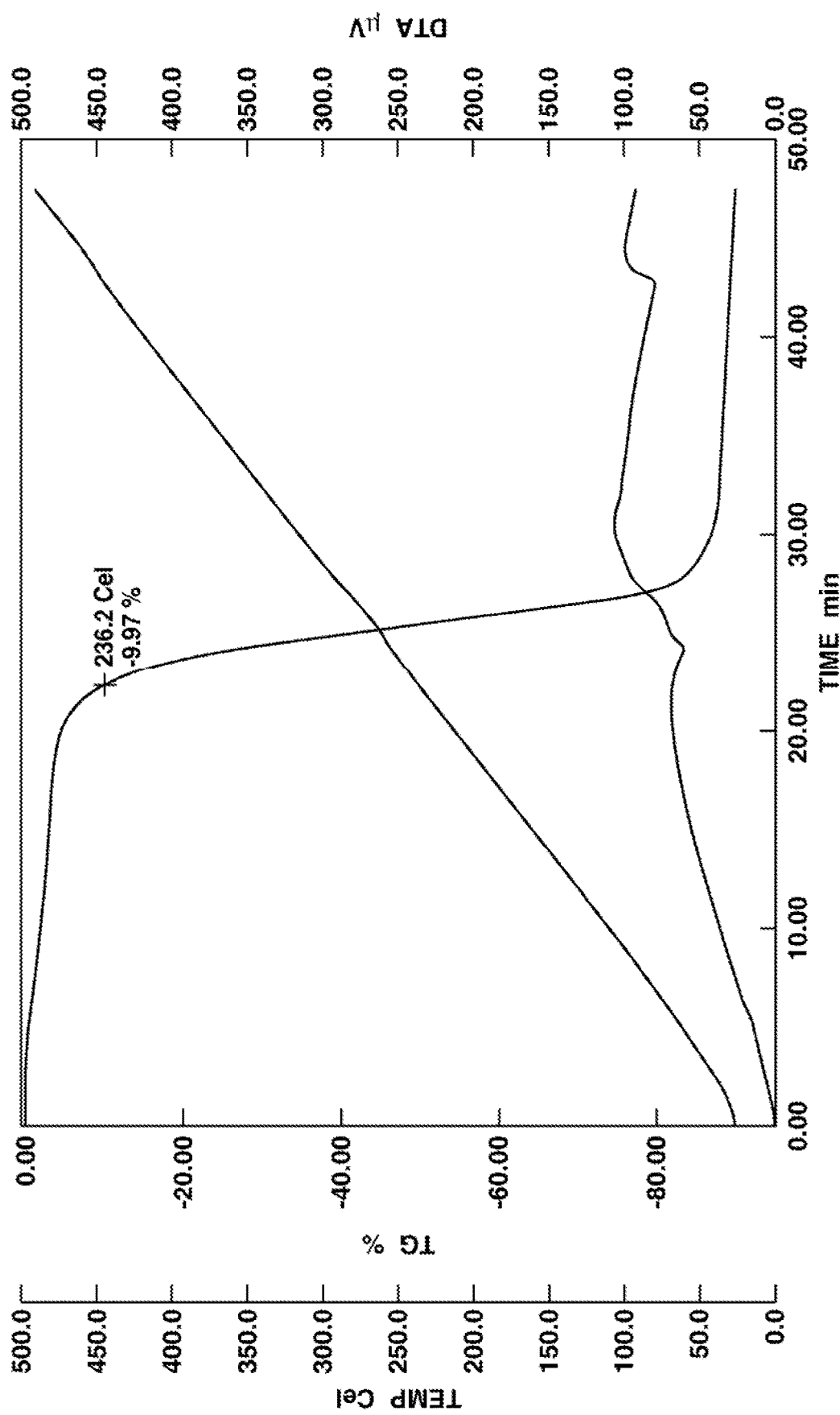
FIG. 9 is the TG-DTA chart of Silicon-Containing Phosphate 1 prepared in Working Example 1.
Figure 10:
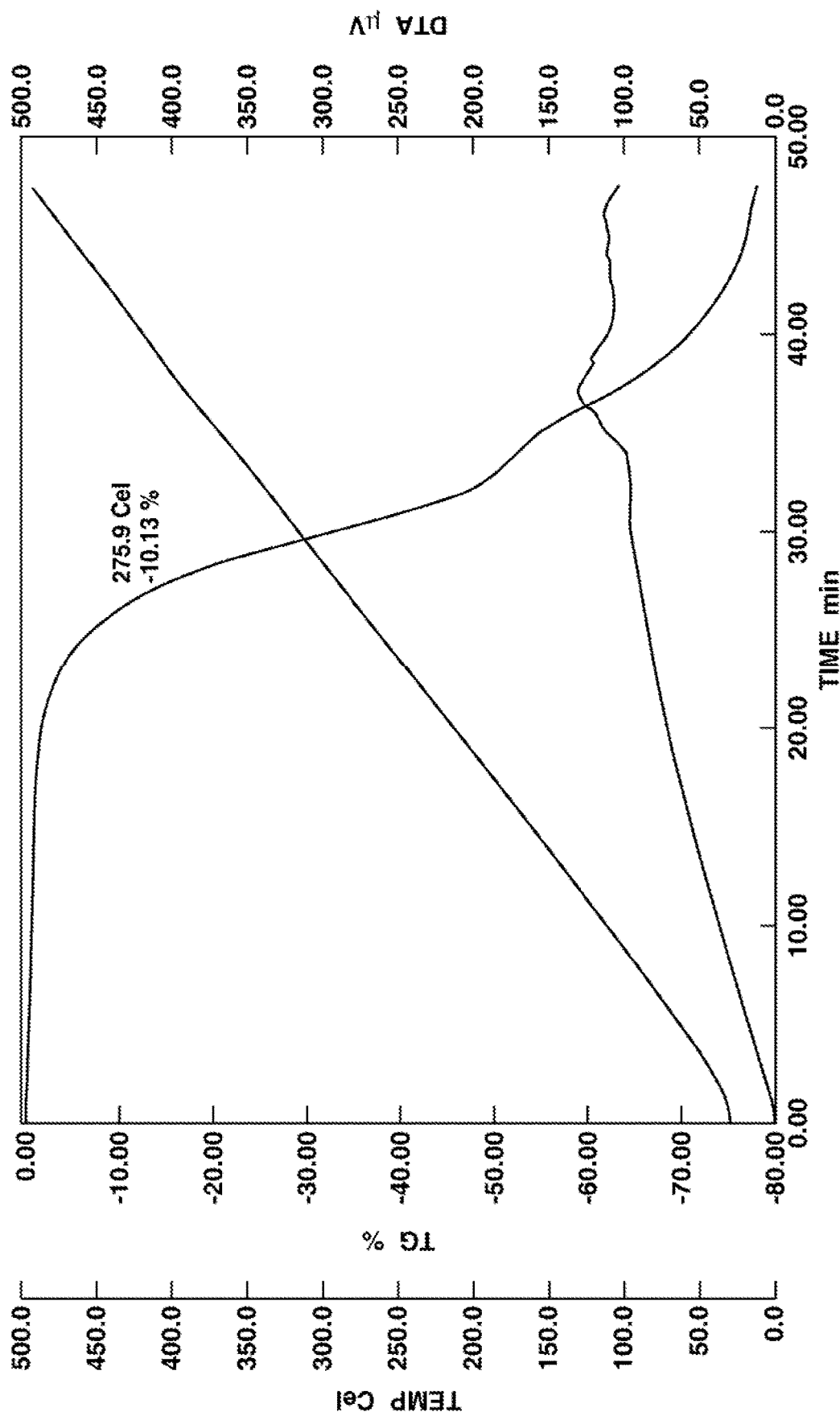
FIG. 10 is the TG-DTA chart of Silicon-Containing Phosphate 2 prepared in Working Example 2.
Figure 11:
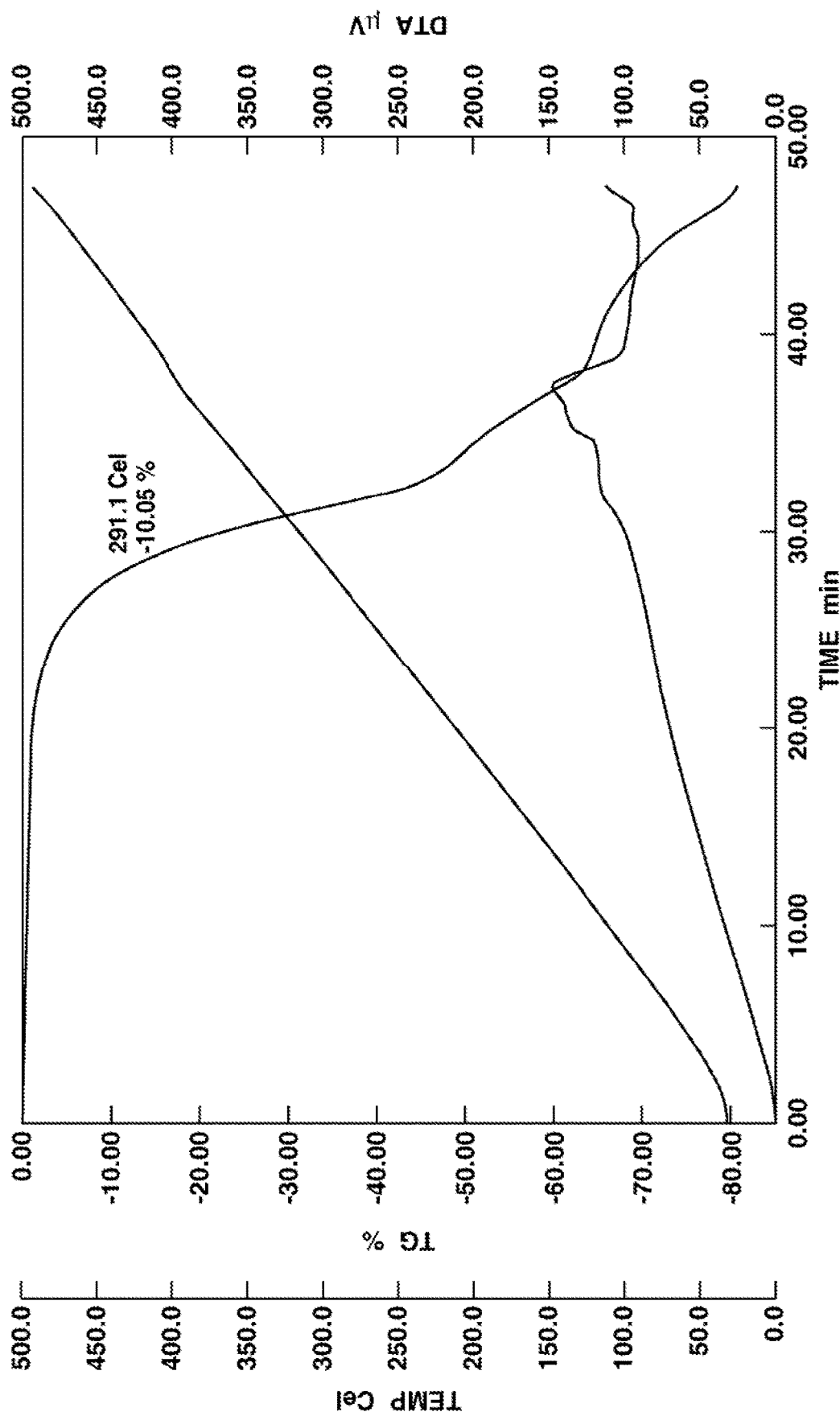
FIG. 11 is the TG-DTA chart of Silicon-Containing Phosphate 3 prepared in Working Example 3.
Figure 12:
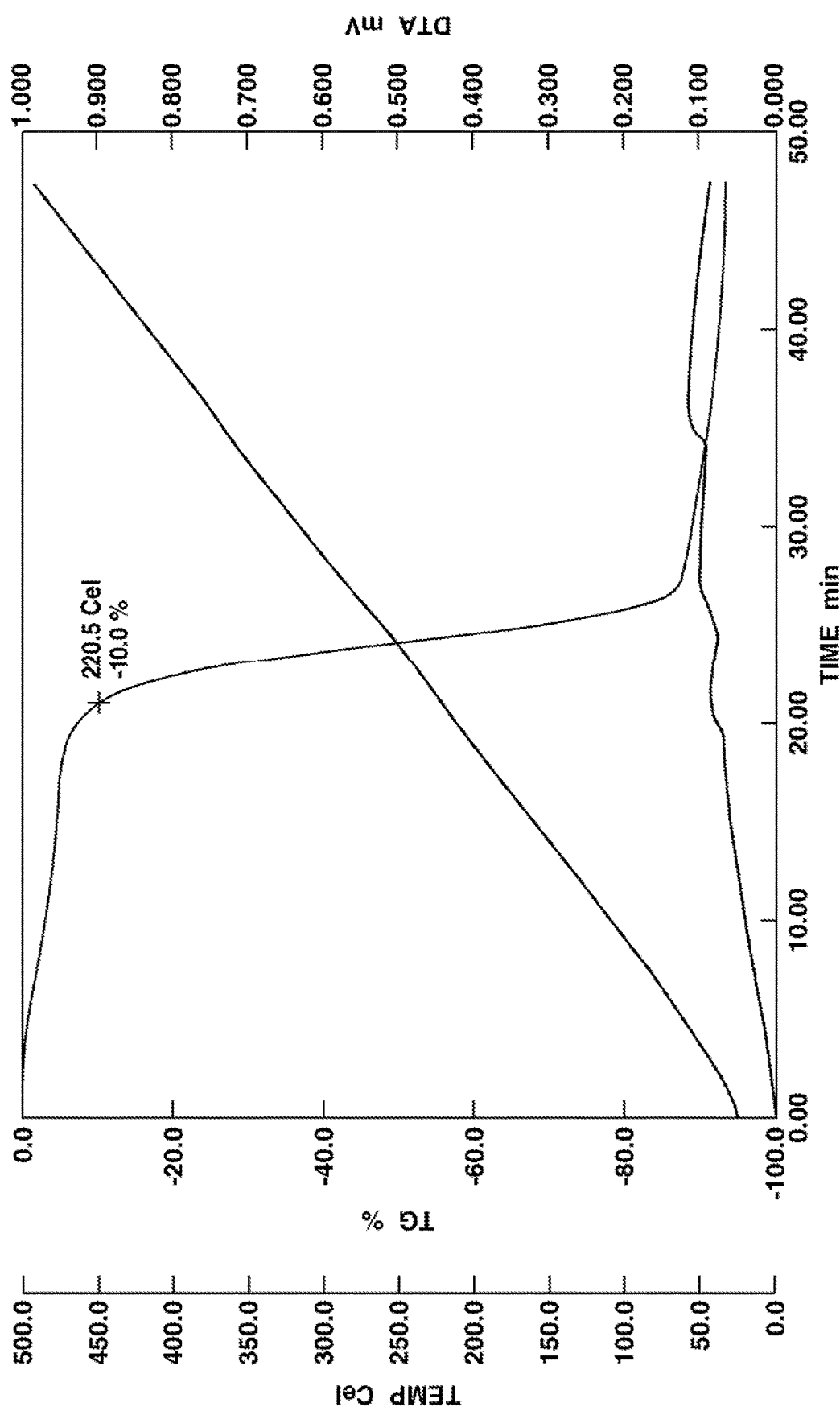
FIG. 12 is the TG-DTA chart of Silicon-Containing Phosphate 4 prepared in Working Example 4.
Figure 13:
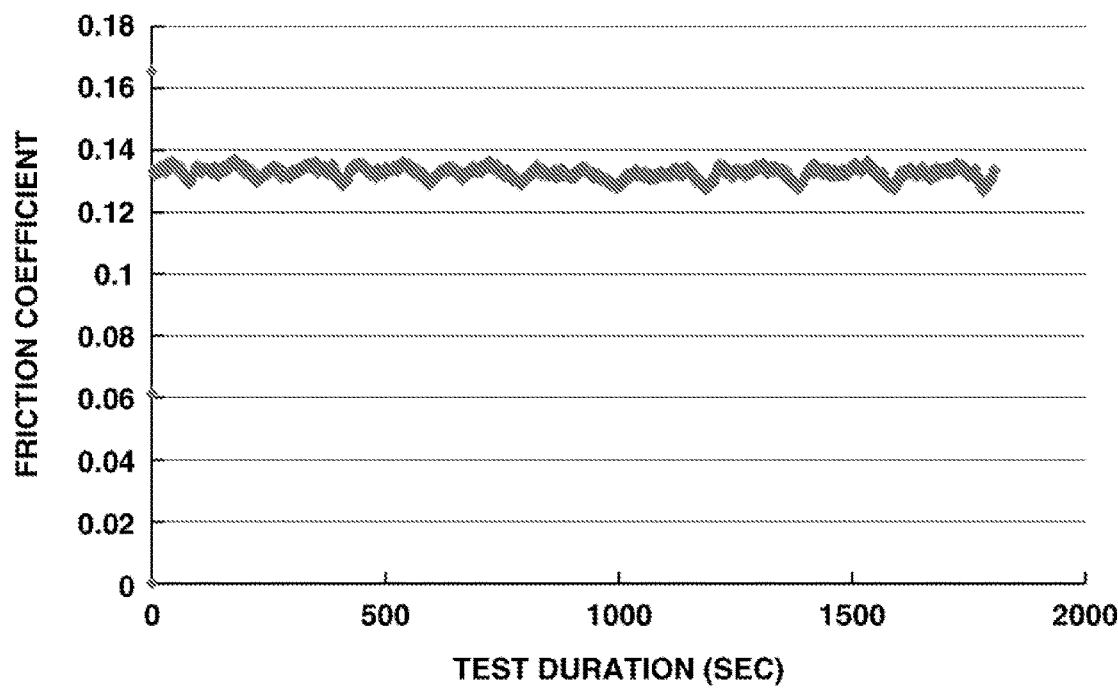
FIG. 13 is a graph showing the change over time in the friction coefficients of Fomblin measured in Comparative Example 1.
Figure 14:
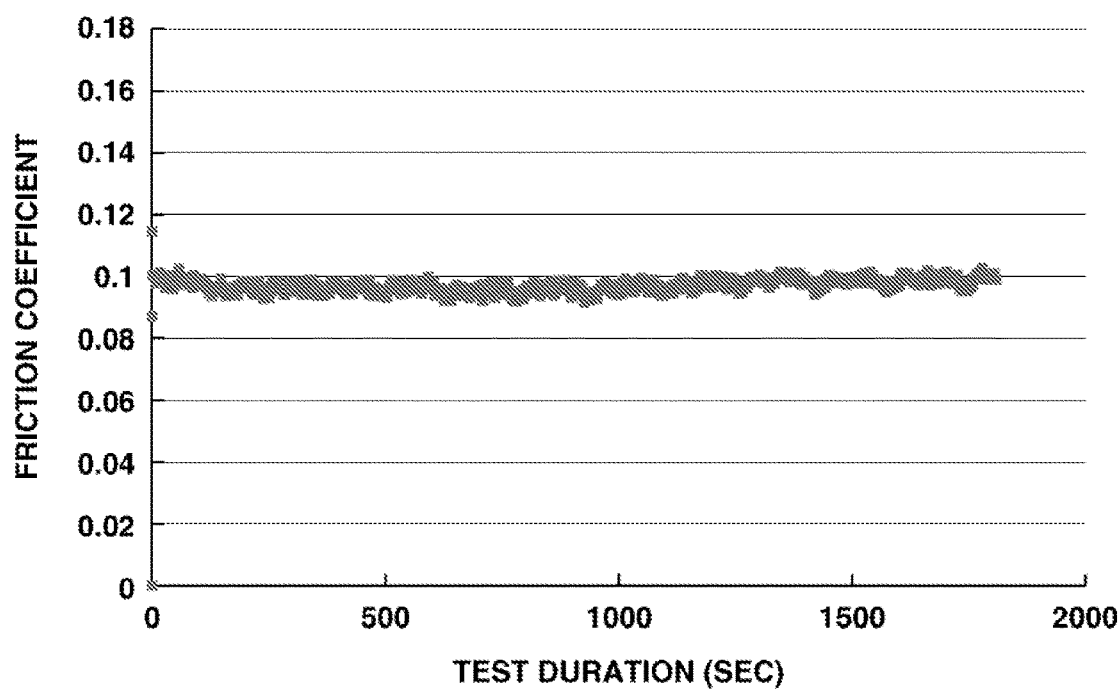
FIG. 14 is a graph showing the change over time in the friction coefficients of to [BMIM] [NTf$_2$] measured in Comparative Example 2.
Figure 15:
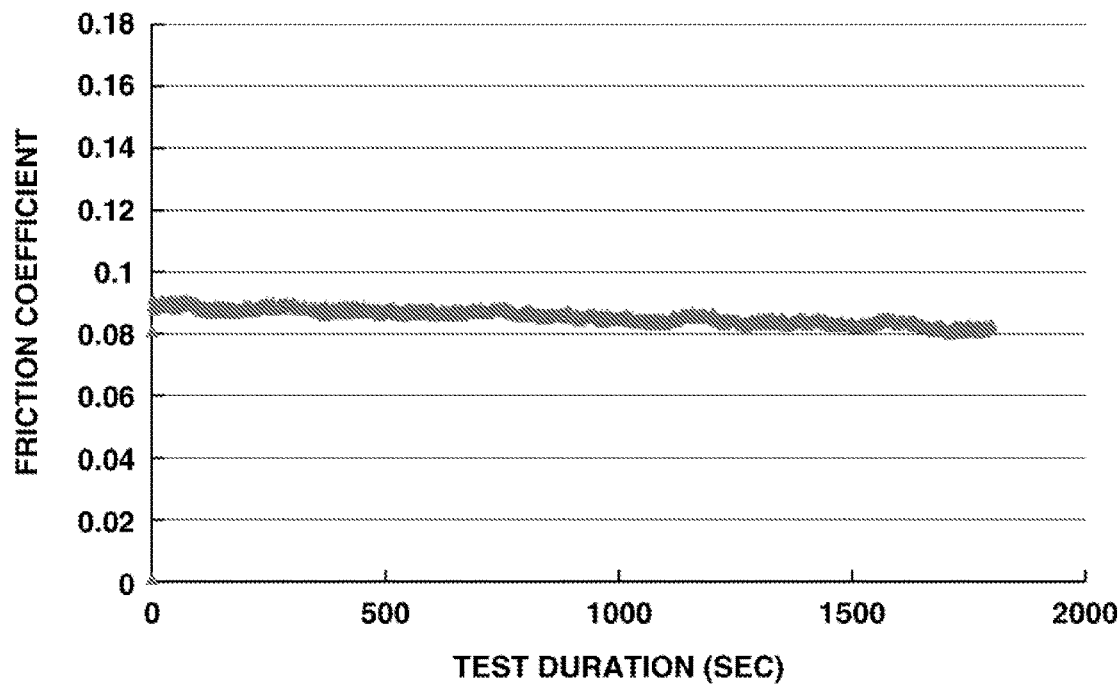
FIG. 15 is a graph showing the change over time in the friction coefficients of Silicon-Containing Phosphate 2 measured in Working Example 5.
Figure 16:
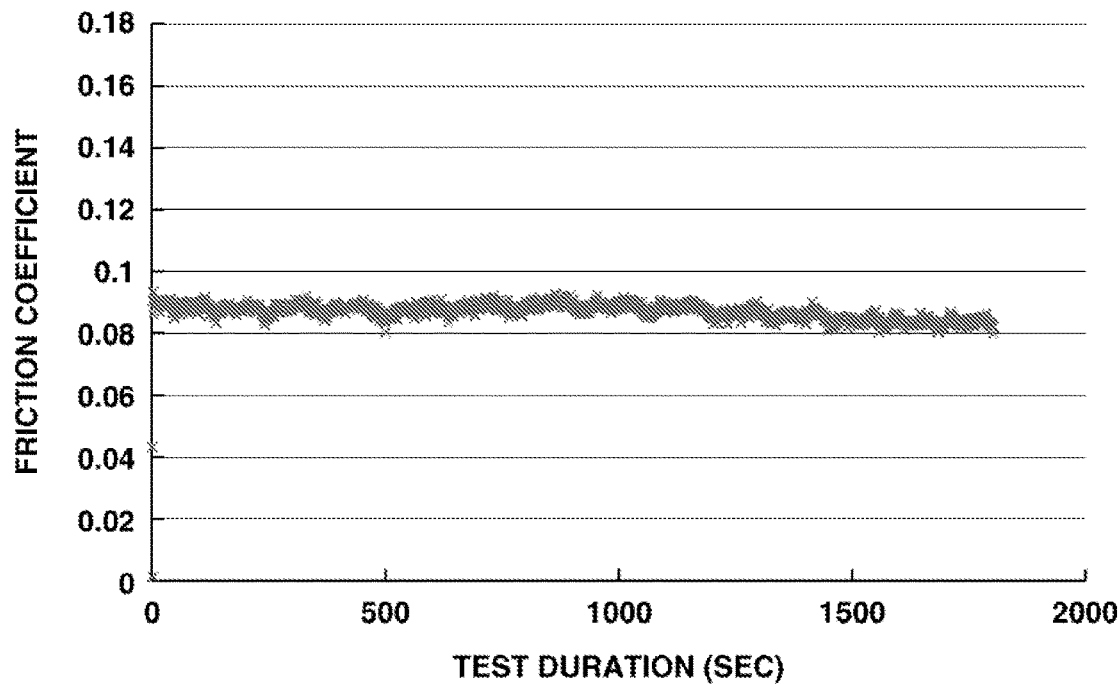
FIG. 16 is a graph showing the change over time in the friction coefficients of Silicon-Containing Phosphate 3 measured in Working Example 6.

Aside from changing N-2-methoxyethylpyrrolidine to triethylamine (Wako Pure Chemical Industries, Ltd.), Silicon-Containing Phosphate 4 (liquid at room temperature) was almost quantitatively obtained in the same way as in Working Example 1. FIG. 4 shows the $^1$H-NMR spectrum of the obtained Silicon-Containing Phosphate 4.

[2] Measurement of Physical Properties of Silicon-Containing Phosphate

The melting points, decomposition points and viscosities of Silicon-Containing Phosphates 1 to 4 were measured. The melting point was measured with the DSC 7000 from Seiko Instruments under the following conditions: the temperature was raised from 20° C. to 50° C. at a rate of 10° C./min and held at 50° C. for 1 minute, then lowered from 60° C. to −70° C. at 1° C./min and held at −70° C. for 1 minute, and subsequently raised from −70° C. to 50° C. at 1° C./min. The decomposition point was measured with the TG-DTA 6200 from Seiko Instruments in an air atmosphere and at a temperature rise rate of 10° C./min from 30 to 500° C. The decomposition point was the temperature at which the weight decreased 10%. The viscosities at 25° C. were measured with a programmable rheometer from Brookfield. The results are shown in Table 1. FIGS. 5 to 8 show the DSC charts of Silicon-Containing Phosphates 1 to 4, respectively, and FIGS. 9 to 12 show the TG-DTA charts, respectively.

TABLE 1

| Silicon-containing phosphate | Melting point (° C.) | Decomposition point (10% weight loss) (° C.) | Viscosity (25° C.) (Pa·s) |
|---|---|---|---|
| 1 | −4 | 236 | 1.425 |
| 2 | 7 | 276 | 0.400 |

TABLE 1-continued

| Silicon-containing phosphate | Melting point (° C.) | Decomposition point (10% weight loss) (° C.) | Viscosity (25° C.) (Pa·s) |
|---|---|---|---|
| 3 | 8 | 291 | 0.575 |
| 4 | 0 | 221 | 3.280 |

[3] Friction Tests

Working Examples 5 to 6, Comparative Examples 1 to 2

The friction coefficients were compared for Silicon-Containing Phosphate 2 (Working Example 5), Silicon-Containing Phosphate 3 (Working Example 6), the commercial perfluoropolyether lubricant Fomblin YL VAC 06/6 (Solvay) (Comparative Example 1), and the commercial ionic liquid butylmethylimidazolium bis(trifluoromethanesulfonyl)imide (Kanto Chemical Co., Ltd.; abbreviated below as [BMIM] [NTf$_2$]) (Comparative Example 2).

Figure 17:
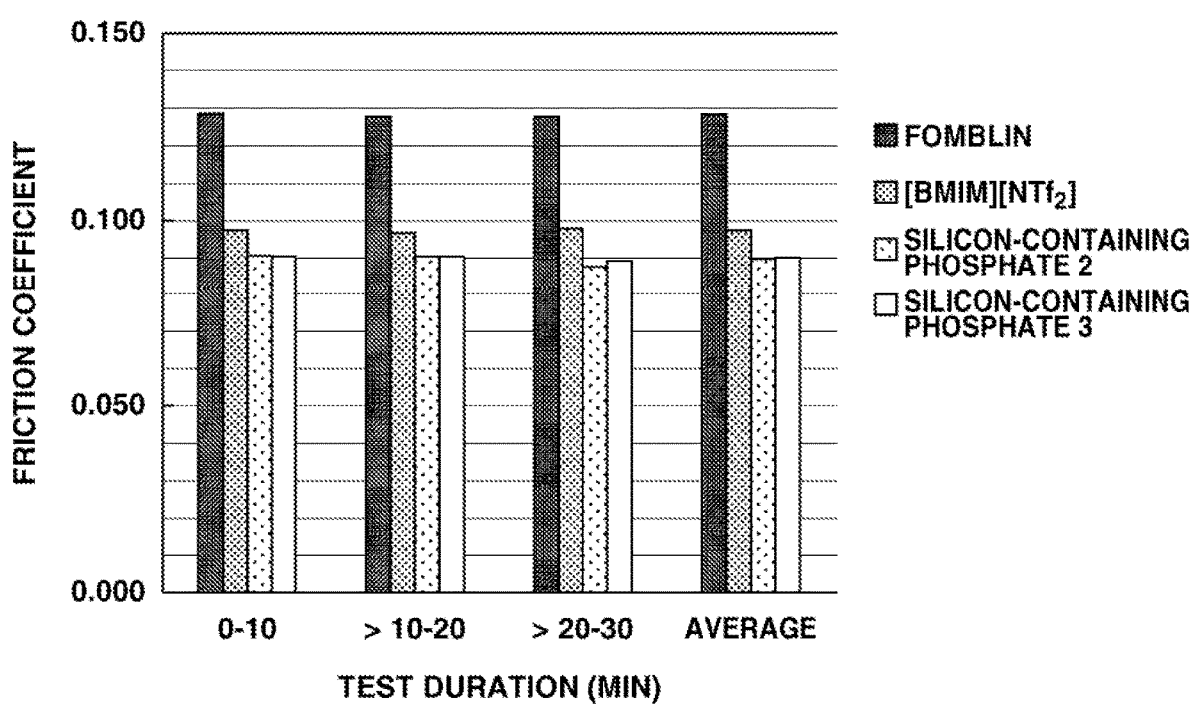
FIG. 17 is a graph showing the average values of the friction coefficients in the ranges of 0 to 10 minutes, 10 minutes to 20 minutes or less, and 20 minutes to 30 minutes or less, of the friction coefficients measured in Working Examples 5 and 6 and Comparative Examples 1 and 2.

The friction test was performed by steel ball to steel disk contact using UMT-TriboLAB (from Bruker), in accordance with ASTM D 6425. Specifically, a test specimen was set in the tester, following which the change over time in friction coefficient was tracked under the conditions in Table 2. The results are shown in FIGS. 13 to 16. Also, the average values of the friction coefficients in the ranges of 0 to 10 minutes, 10 minutes to 20 minutes or less, and 20 minutes to 30 minutes or less, of the friction coefficients are shown in Table 3. Moreover, FIG. 17 shows a graph of the results of Table 3.

TABLE 2

| | | |
|---|---|---|
| Measurement conditions | Load (N) | 100 |
| | Oscillation frequency (Hz) | 50 |
| | Stroke (mm) | 1.00 |
| | Test temperature (° C.) | 25 |
| | Test duration (min) | 30 |
| Ball | Material | AISI 52100 (chrome steel) |
| | Size (mm) | φ 10 |
| Disk | Material | AISI 52100 (chrome steel) |
| | Size (mm) | φ 24 × 7.9 |

TABLE 3

| | | Measurement duration (min) | | | |
|---|---|---|---|---|---|
| | | 0-10 | >10-20 | >20-30 | Average |
| Comparative Example 1 | Fomblin | 0.1286 | 0.1279 | 0.1276 | 0.1280 |
| Comparative Example 2 | [BMIM] [NTf$_2$] | 0.0976 | 0.0967 | 0.0981 | 0.0975 |
| Working Example 5 | Silicon-Containing Phosphate 2 | 0.0908 | 0.0905 | 0.0876 | 0.0896 |
| Working Example 6 | Silicon-Containing Phosphate 3 | 0.0905 | 0.0905 | 0.0892 | 0.0901 |

Silicon-Containing Phosphates 2 and 3 both had low friction coefficients, and also exhibited low friction coefficients that were lower than even the existing ionic liquid [BMIM] [NTf$_2$], which is one type of ionic liquid having the anion NTf$_2^-$ that is regarded to have a good performance as a lubricant. It is apparent from the above that the lubricants of the invention have an excellent performance.

The invention claimed is:

1. A salt comprising a silicon-containing phosphate anion of formula (1) below:

[Chem. 1]

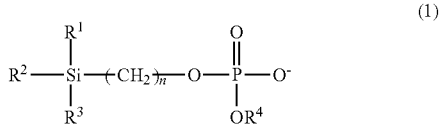

(1)

wherein R$^1$ to R$^4$ are each independently an alkyl group of 1 to 4 carbon atoms, and n is an integer of 2 to 8.

2. The salt of claim 1, wherein R$^1$ to R$^3$ are the same group.

3. The salt of claim 2, wherein R$^1$ to R$^3$ groups are all methyl groups.

4. The salt of claim 1, wherein R$^4$ is a methyl group.

5. The salt of claim 1, wherein n is an integer of 2 to 4.

6. The salt of claim 1, wherein the cation is an organic cation.

7. The salt of claim 1, wherein the cation is a phosphorus atom-containing cation.

8. The salt of claim 1, wherein the cation is a nitrogen atom-containing cation.

9. The salt of claim 1, which is an ionic liquid having a melting point of 100° C. or below.

10. A composition comprising the salt of claim 1.

11. A lubricant comprising the salt of claim 1.

12. A silicon-containing phosphoric acid ester of formula below

[Chem. 2]

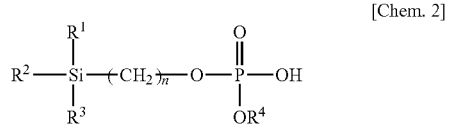

wherein R$^1$ to R$^4$ are each independently an alkyl group of 1 to 4 carbon atoms, and n is an integer of 2 to 8.

* * * * *